United States Patent [19]

Fukuda et al.

[11] Patent Number: 5,331,076

[45] Date of Patent: *Jul. 19, 1994

[54] SILOXANE COMPOUNDS

[75] Inventors: Kenichi Fukuda; Yasuo Tarumi, both of Takasaki; Hiroshi Inomata, Annaka; Yasushi Yamamoto, Takasaki, all of Japan

[73] Assignee: Shin-Etsu Chemical Co., Ltd., Tokyo, Japan

[*] Notice: The portion of the term of this patent subsequent to Mar. 23, 2010 has been disclaimed.

[21] Appl. No.: 993,877

[22] Filed: Dec. 23, 1992

[30] Foreign Application Priority Data

Dec. 24, 1991 [JP] Japan .................. 3-356414

[51] Int. Cl.$^5$ .................. C08L 83/08; C07F 7/08
[52] U.S. Cl. .................. 528/27; 528/42; 549/215
[58] Field of Search .............. 356/434, 445; 549/215; 528/42, 15, 27, 25

[56] References Cited

U.S. PATENT DOCUMENTS

| | | | |
|---|---|---|---|
| 3,542,830 | 11/1970 | Kim | 556/434 |
| 3,627,801 | 12/1971 | Pierce et al. | 556/434 |
| 3,647,740 | 3/1972 | Loree et al. | 556/434 |
| 3,818,064 | 6/1974 | Kim | 556/434 |
| 4,057,566 | 11/1977 | Carter et al. | 556/434 |
| 5,196,558 | 3/1993 | Inomata et al. | 547/215 |

FOREIGN PATENT DOCUMENTS

| | | |
|---|---|---|
| 0208239 | 1/1987 | European Pat. Off. . |
| 0311262 | 4/1989 | European Pat. Off. . |
| 0435654 | 7/1991 | European Pat. Off. . |
| 2648242 | 8/1977 | Fed. Rep. of Germany . |

*Primary Examiner*—Ralph H. Dean
*Attorney, Agent, or Firm*—Millen, White, Zelano, & Branigan

[57] ABSTRACT

Novel siloxane compounds having a fluorinated group, an SiH group reactive with silicone resins, and an epoxy-bearing organic group attached to a silicon atom, each in a backbone, are effective for providing adhesion and are useful tackifiers for various resins.

13 Claims, No Drawings

SILOXANE COMPOUNDS

BACKGROUND OF THE INVENTION

1. Field of the Invention

This invention relates to novel siloxane compounds effective for imparting adhesion to silicone resins or the like and thus bonding silicone resins or the like to various members. More particularly, it relates to siloxane compounds having a fluorinated group in a backbone and effective for imparting adhesion to fluorinated silicone resins and rubbers.

2. Prior Art

Several siloxane compounds are known to impart adhesion to silicone resins. For example, Japanese Patent Application Kokai Nos. 47605/1987, 47608/1987 and 49305/1987 discloses hydrogensiloxanes having a perfluoropolyether or perfluoroalkylene group in a backbone and containing at least two SiH groups in a molecule. These hydrogensiloxanes are represented by the following formula (5):

$$(HSiO)_k \underset{\underset{CH_3}{|}}{\overset{\overset{(CH_3)_{3-k}}{|}}{\underset{|}{Si}}} CH_2CH_2R^f CH_2CH_2 \underset{\underset{CH_3}{|}}{\overset{\overset{(CH_3)_{3-k}}{|}}{\underset{|}{Si}}} (OSiH)_k \quad (5)$$

wherein $R^f$ is a perfluoropolyether or perfluoroalkylene group and k is equal to 1, 2 or 3.

These siloxane compounds, however, could not impart satisfactory adhesion to fluorinated silicone resins. It is thus desired to have a siloxane compound capable of imparting satisfactory adhesion to fluorinated silicone resins.

SUMMARY OF THE INVENTION

An object of the present invention is to provide a novel and improved siloxane compound which has good affinity to fluorinated silicone resins and rubbers and greatly contributes to solvent resistance and minimal water permeability.

The inventors have found that a novel siloxane compound of the following formula (1) is obtained by effecting addition reaction between a hydrogensiloxane of the following formula (6) and an epoxy compound having an aliphatic double bond in amounts of 1 to 5 equivalents.

$$(XSiO)_p(HSiO)_q R^1{}_{3-p-q} SiCH_2CH_2 R^f CH_2CH_2 SiR^1{}_{3-m-n}(OSiH)_m(OSiX)_n \quad$$

In formula (1), $R^f$ is a perfluoropolyether or perfluoroalkylene group, $R^1$ is a monovalent lower hydrocarbon group or a group of the following formula (2):

$$-O\underset{\underset{CH_3}{|}}{\overset{\overset{CH_3}{|}}{Si}}CH_2CH_3. \quad (2)$$

X is a group of the following formula (3):

$$-R^2-CH\underset{\diagdown}{\overset{\diagup O \diagdown}{\phantom{X}}}CH_2. \quad (3)$$

wherein $R^2$ is a divalent organic group, or a group of the following formula (4):

$$-CH_2-CH_2-\underset{\text{(cyclohexyl epoxide)}}{\bigcirc\!\!\!\!\!\!\diagup\!\!\!\diagdown\!\!O} \quad (4)$$

letters p, q, m and n are integers of 0 to satisfying the relationship: $0 < p+q \leq 3$, $0 < m+n \leq 3$, $0 < p+n$, $0 < q+m$, $0 < p+q+m+n < 6$.

$$(HSiO)_r SiCH_2CH_2R^f CH_2CH_2 Si(OSiH)_s \quad (6)$$

In formula (6), $R^f$ and $R^1$ are as defined above, and letters r and s are integers of 0 to 3 satisfying the relationship: $0 < r+s < 6$.

The siloxane compounds of formula (1), that is, siloxane compounds containing at least one hydrogen atom attached to a silicon atom reactive with silicone resins (SiH group) and at least one epoxy-bearing organic group attached to a silicon atom participating in bonding to substrates or adherents, each in a molecule, have high affinity to fluorinated silicone resins and rubbers and greatly contribute to solvent resistance and minimal water permeability. Therefore, the compounds are useful tackifiers for imparting adhesion to fluorinated silicone resins and rubbers.

DETAILED DESCRIPTION OF THE INVENTION

The siloxane compounds of the present invention are represented by formula (1).

$$(XSiO)_p(HSiO)_q R^1{}_{3-p-q} SiCH_2CH_2 R^f CH_2CH_2 SiR^1{}_{3-m-n}(OSiH)_m(OSiX)_n$$

In formula (1), $R^f$ is a perfluoropolyether group or perfluoroalkylene group. Preferably, the perfluoropolyether groups have 4 to 15 carbon atoms and are typically represented by the following formulae (7) and (8).

$$-CF(OCF_2CF)_x OCF_2CF_2O(CFCF_2O)_y CF- \quad (7)$$
$$\phantom{-CF(OCF_2CF)_xOCF_2CF_2O(CFCF_2O)_y}|\phantom{CF-}$$
Y is F or $CF_3$, and letters x and y are equal to 0, 1 or 2, meeting $0 \leq x+y \leq 3$.

$$-CF_2CF_2(OCF_2CF)_x O(CF_2)_z O(CFCF_2O)_y CF_2CF_2- \quad (8)$$

Y, x and y are as defined above, and z is an artitrary integer, preferably from 1 to 6.

Examples of the perfluoropolyether group are given below.

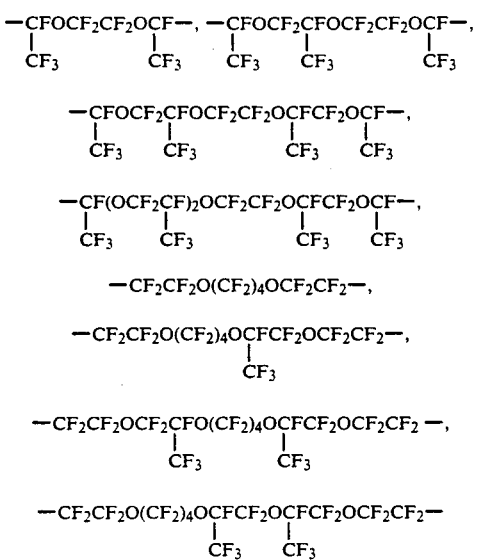

The perfluoroalkylene groups represented by $R^f$ preferably have 2 to 10 carbon atoms and typically represented by the following formula:

$$-C_wF_{2w}- \quad (9)$$

wherein w is an integer of 2 to 10. Examples include $-C_2F_4-$, $-C_4F_8-$, $-C_6F_{12}-$, and $-C_8F_{16}-$.

$R^1$ is a monovalent lower hydrocarbon group such as methyl and ethyl or a group of formula (2):

X is a group of formula (3) or (4).

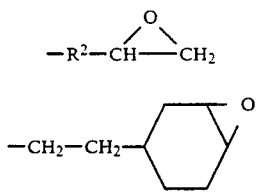

In formula (3), $R^2$ is a divalent organic group, which is not particularly limited although it is preferably a lower alkylene group having 1 to 6 carbon atoms which may have a terminal or intervening oxygen atom. Divalent organic groups containing an ester bond are also acceptable. Examples are $-(CH_2)_4-$, $-(CH_2)_2OCH_2-$, $-CH_2CH_2-$, $-(CH_2)_3O-$, and $-(CH_2)_3OCH_2-$.

Letters p, q, m and n are integers of 0 to 3, satisfying the relationship: $0<p+q\leq 3$, $0<m+n\leq 3$, $0<p+n$, $0<q+m$, and $0<p+q+m+n<6$.

This implies that the siloxane compounds of formula (1) have in a molecule at least one hydrogen atom attached to a silicon atom (or at least one SiH group) and at least one epoxy-bearing organic group attached to a silicon atom.

The siloxane compounds of the present invention can be synthesized by effecting addition reaction between an organohydrogen-siloxane and an aliphatic double bond-containing epoxy compound, that is, between a SiH bond in the former and an aliphatic double bond in the latter, in the presence of a platinum series catalyst.

One of the starting reactants is a hydrogensiloxane which is preferably of the general formula (6):

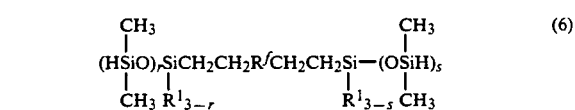

wherein $R^f$ and $R^1$ are as defined above and r and s are integers of 0 to 3, satisfying $0<r+s<6$.

Preferred examples of the aliphatic double bond-containing epoxy compound are given by the following formulae (10) to (12).

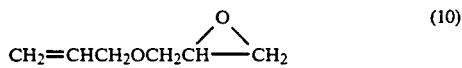

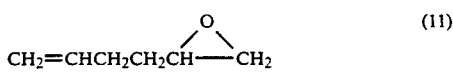

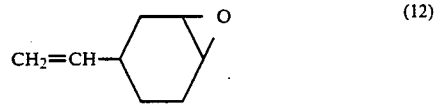

The addition reaction between the hydrogensiloxane of formula (6) and the aliphatic double bond-containing epoxy compound of formulae (10) to (12) may be carried out in a conventional manner using well-known addition reaction catalyst, typically platinum and platinum compounds. The reaction temperature is generally 40° to 100° C., preferably 60° to 75° C.

Although the addition reaction may be carried out without solvent, the use of a solvent is preferred for reaction temperature control. Any solvent which does not give rise to side reaction with SiH and epoxy groups or adversely affect the catalyst may be used although those solvents which permit addition reaction under atmospheric pressure are preferred, for example, aromatic hydrocarbons such as benzene, toluene and xylene, and fluorinated aromatic compounds such as benzotrifluoride and n-xylenehexafluoride. At the end of addition reaction, the reaction product may be purified by removing the catalyst through adsorption on activated carbon or the like and distilling off the solvent.

The siloxane compounds of the invention contain a fluorinated group, an SiH group reactive with silicone resins, and an epoxy-bearing organic group attached to a silicon atom participating in bonding to substrates or adherents, each in a backbone, so that they have high affinity to silicone reins and rubbers, especially fluorinated silicone resins and rubbers and thus provide good adhesion thereto.

EXAMPLE

Examples of the present invention are given below by way of illustration and not by way of limitation.

EXAMPLE 1

A 200-ml flask equipped with a condenser and thermometer was charged with 50 grams (0.045 mol) of a hydrogensiloxane of formula (13) and 50 grams of toluene and heated to a temperature of 60° C. With thorough stirring, 0,088 gram of a toluene solution containing a 2-ethyl-hexanol-modified platinum catalyst having a platinum concentration of 0.5% (Pt: $2.5 \times 10^{-6}$ mol) was added dropwise to the flask, and thereafter, 30.3 grams of a toluene solution containing 10.3 grams (0,090 mol) of an epoxy compound of formula (10) was added dropwise over 20 minutes.

Mass spectrometry
 1340 (M+)
IR absorption spectrum

There appeared a characteristic absorption peak attributable to a SiH group at wavenumber 2140 cm$^{-1}$ and a characteristic absorption peak attributable to an epoxy group (C—H) at wavenumber 3000–3080 cm$^{-1}$.
SiH content
 Calcd.: 0.0015 mol/g Found: 0. 0014 mol/g

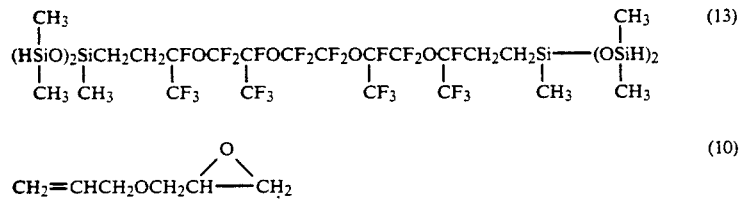

The reaction mixture was allowed to age at 60° C. for 30 minutes and then to cool down, shaken for 1 hour together with activated carbon, removed of the activated carbon by filtration, and subjected to vacuum distillation at 70° C. and 1 mmHg for one hour for toluene removal, obtaining 58.5 grams of a product. The product was analyzed by gel permeation chromatography (GPC) to find that it contained 27.5 grams of a di-adduct (yield 46%).

The di-adduct isolated and collected by GPC was analyzed by proton-NMR, mass spectroscopy, IR absorption spectroscopy, elemental analysis and Si—H content measurement. As a result of these analyses, it was identified to be a mixture of compounds have the structure of formula (14) wherein a and b are integers of 0 to 2, meeting a+b=2.

$^1$H-NMR spectrum 4.58~4.93 ppm (Si—H, m, 2H)
0.13~0.56 ppm (Si—CH$_3$, m, 30H)
0.66~1.08 ppm (Si—CH$_2$—, m, 8H)
1.72~2.41 ppm (C—CH$_2$—CF, m, 4H)
3.43~4.00 ppm (C—CH$_2$—O, m, 8H)
1.21~1.65 ppm (C—CH$_2$—C, m, 4H)
2.94~3.28 ppm (—CH——C, m, 2H)
  \_O_/
2.45~2.88 ppm (C——CH$_2$, m, 4H)
  \_O_/

EXAMPLE 2

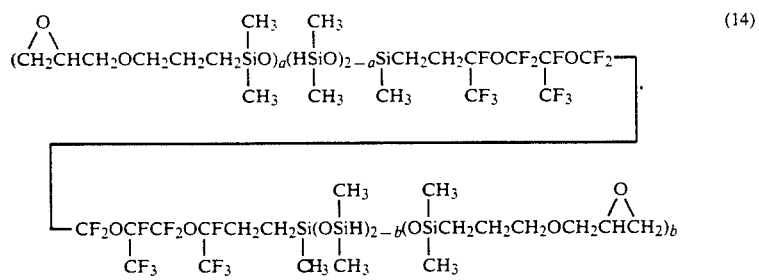

Elemental analysis

|  | C | H | Si | F |
|---|---|---|---|---|
| Calcd.* (%) | 34.18 | 4.68 | 12.62 | 34.14 |
| Found (%) | 33.97 | 4.81 | 12.55 | 34.96 |

*calculated as C$_{38}$H$_{62}$F$_{24}$O$_{12}$Si$_6$

A reactor as used in Example 1 was charged with 73 grams (0.057 mol) of a hydrogensiloxane of formula (15) and 70 grams of toluene. In a similar manner as in Example 1, 0.105 grams of a platinum catalyst toluene solution (Pt: $2.7 \times 10^{-6}$ mol) was added dropwise to the reactor, and thereafter, 34.3 grams of a toluene solution containing 14.3 grams (0.125 mol) of an epoxy compound of formula (10) was added dropwise over 30 minutes.

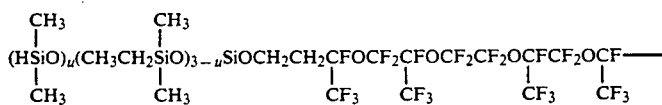

(15)

In the formula, u and v are integers of 1 to 3, meeting u+v=4.

By following the same procedure as in Example 1, there was obtained 84.1 grams of a product. The product was analyzed by GPC to find that it contained 237.0 grams of a di-adduct (yield 37%). The di-adduct isolated and collected by GPC was identified by analysis to be a mixture of compounds having the structure of formula (16) wherein a, b, c and d are integers of 0 to 2, meeting $a+c=2$, $b+d=2$, $1 \leq a+b \leq 3$ and $1 \leq c+d \leq 3$.

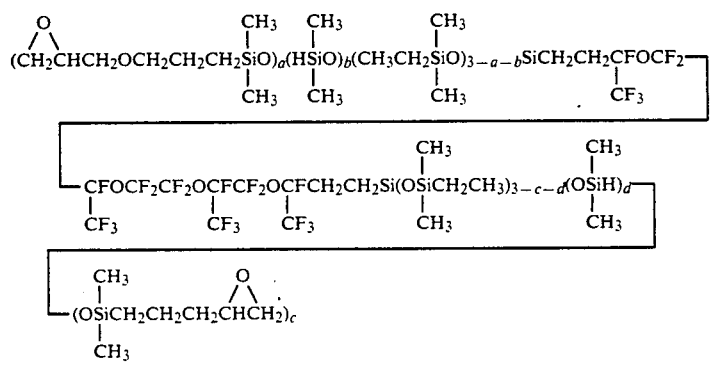

(16)

Elemental analysis

|  | C | H | Si | F |
|---|---|---|---|---|
| Calcd.* (%) | 34.96 | 5.20 | 14.86 | 30.16 |
| Found (%) | 34.23 | 4.89 | 15.21 | 29.96 |

*calculated as $C_{44}H_{78}F_{24}O_{14}Si_{18}$

Mass spectrometry.
1510 (M+)

IR absorption spectrum

There appeared a characteristic absorption peak attributable to a SiH group at wavenumber 2140 cm$^{-1}$ and a characteristic absorption peak attributable to an epoxy group (C—H) at wavenumber 3000 to 3080 cm$^{-1}$.

SiH content
Calcd.: 0.0013 mol/g  Found: 0.0014 mol/g $^1$H-NMR spectrum

| | |
|---|---|
| 4.58~4.95 ppm | (Si—H, m, 2H) |
| 0.11~0.49 ppm | (Si—CH$_3$, m, 36H) |
| 0.66~1.14 ppm | (Si—CH$_2$—, m, 12H) |
| 1.66~2.35 ppm | (C—CH$_2$—CF, m, 4H) |
| 3.41~4.00 ppm | (C—CH$_2$—O, m, 4H) |
| 1.27~1.71 ppm | (C—CH$_2$—C, m, 4H) |
| 3.01~3.35 ppm | (—CH——C, m, 2H) $\diagdown O \diagup$ |
| 2.44~2.91 ppm | (C——CH$_2$, m, 4H) $\diagdown O \diagup$ |

EXAMPLE 3

A reactor as used in Example 1 was charged with 50 grams (0.067 mol) of a hydrogensiloxane of formula (17) and 70 grams of toluene. In a similar manner as in Example 1, 0.131 grams of a platinum catalyst toluene solution (Pt: 3.35×10$^{-6}$ mol) was added dropwise to the reactor, and thereafter, 35.3 grams of a toluene solution containing 15.3 grams (0.134 mol) of an epoxy compound of formula (10) was added dropwise over 30 minutes.

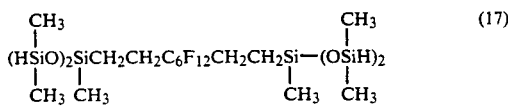

(17)

(10)

By following the same procedure as in Example 1, there was obtained 61.8 grams of a product. The product was analyzed by GPC to find that it contained 31.2 grams of a di-adduct (yield 48%). The di-adduct isolated and collected by GPC was identified by analysis to be a mixture of compounds having the structure of formula (18) wherein a and b are integers of 0 to 2, meeting $a+b=2$.

$$\text{(CH}_2\text{CHCH}_2\text{OCH}_2\text{CH}_2\text{CH}_2\text{SiO})_a(\text{HSiO})_2\text{—}a\text{SiCH}_2\text{CH}_2\text{C}_6\text{F}_{12}\text{CH}_2\text{CH}_2\text{—} \quad (18)$$

(with CH₃ substituents and terminal —Si(OSiH)₂₋ᵦ(OSiCH₂CH₂CH₂OCH₂CHCH₂)ᵦ group with epoxy O)

Elemental analysis

|        | C     | H    | Si    | F     |
|--------|-------|------|-------|-------|
| Calcd.* (%) | 39.57 | 6.43 | 17.35 | 23.47 |
| Found (%)   | 39.19 | 6.75 | 16.98 | 22.04 |

*calculated as $C_{32}H_{62}F_{12}O_8Si_6$

Mas spectrometry
970 (M+)
IR absorption spectrum

There appeared a characteristic absorption peak attributable to a SiH group at wavenumber 2140 cm$^{-1}$ and a characteristic absorption peak attributable to an epoxy group (C—H) at wave-number 3000 to 3080 cm$^{-1}$.

SiH content
Calcd.: 0.0021 mol/g  Found: 0.0020 mol/g
$^1$H-NMR spectrum

| | |
|---|---|
| 4.49~4.85 ppm | (Si—H. m, 2H) |
| 0.05~0.41 ppm | (Si—CH₃, m, 30H) |
| 0.41~1.05 ppm | (Si—CH₂—, m, 8H) |
| 1.80~2.52 ppm | (C—CH₂—CF, m, 4H) |
| 3.16~3.54 ppm | (C—CH₂—C, m, 4H) |
| 1.45~1.76 ppm | (C—CH₂—O, m, 8H) |
| 2.79~3.69 ppm | (—CH—C, m, 2H) with O |
| 2.28~2.66 ppm | (C—CH₂, m, 4H) with O |

There have been described novel siloxane compounds which are effective for imparting adhesion to a wide variety of resins. They are useful tackifiers for imparting adhesion to not only conventional resins, but also fluorinated silicone resins and rubbers since they have good affinity to fluorinated silicone resins and rubbers by virtue of the inclusion of a fluorinated group. They also make a great contribution to solvent resistance and minimal water permeability.

Although some preferred embodiments have been described, many modifications and variations may be made thereto in the light of the above teachings. It is therefore to be understood that within the scope of the appended claims, the invention may be practiced otherwise than as specifically described.

We claim:

1. A siloxane compound of formula (1):

$$(\text{XSiO})_p(\text{HSiO})_q\text{R}^1{}_3\text{—}p\text{—}q\text{SiCH}_2\text{CH}_2\text{R}^f\text{CH}_2\text{CH}_2\text{SiR}^1{}_3\text{—}m\text{—}n(\text{OSiH})_m(\text{OSiX})_n$$

(with CH₃ substituents)

wherein R$^f$ is a perfluoropolyether or perfluoroalkylene group;

R$^1$ is a monovalent lower hydrocarbon group or a group of formula (2):

$$-\text{OSiCH}_2\text{CH}_3 \quad (2)$$
(with CH₃ substituents)

X is a group of formula (3):

$$-\text{R}^2-\text{CH}\underset{O}{\overset{}{—}}\text{CH}_2 \quad (3)$$

wherein R$^2$ is a divalent organic group, or a group of formula (4):

$$-\text{CH}_2-\text{CH}_2-\overset{\text{cyclohexyl-O}}{\phantom{X}} \quad (4)$$

and letters p, q, m and n are integers of 0 to 3 satisfying the relationship: $0 < p+q \leq 3$, $0 < m+n \leq 3$, $0 < p+n$, $0 < q+m$, $0 < p+q+m+n < 6$.

2. A compound according to claim 1, wherein R$^f$ is a perfluoropolyether group having 4–15 carbon atoms.

3. A compound according to claim 1, wherein R$^f$ is of the formula $$-\text{CF}(\text{OCF}_2\text{CF})_x\text{OCF}_2\text{CF}_2\text{O}(\text{CFCF}_2\text{O})_y\text{CF}-$$
(with Y substituents)

wherein Y is F or CF₃; x is 0, 1 or 2; y is 0, 1 or 2; and the sum of x+y satisfies the equation $0 \leq +y \leq 3$.

4. A compound according to claim 1, wherein R$^f$ is of the formula $$-\text{CF}_2\text{CF}_2(\text{OCF}_2\text{CF})_x\text{O}(\text{CF}_2)_z\text{O}(\text{CFCF}_2\text{O})_y\text{CF}_2\text{CF}_2-$$
(with Y substituents)

wherein Y is F or CF₃; z is 1–6; x is 0, 1 or 2; y is 0, 1 or 2; and the sum of x+y satisfies the equation $0 \leq x+y \leq 3$.

5. A compound according to claim 1, wherein R$^f$ is selected from the following formulae:

$$-\text{CFOCF}_2\text{CF}_2\text{OCF}-, \quad -\text{CFOCF}_2\text{CFOCF}_2\text{CF}_2\text{OCF}-,$$
(with CF₃ substituents)

$$-\text{CFOCF}_2\text{CFOCF}_2\text{CF}_2\text{OCFCF}_2\text{OCF}-,$$
(with CF₃ substituents)

$$-\text{CF}(\text{OCF}_2\text{CF})_2\text{OCF}_2\text{CF}_2\text{OCFCF}_2\text{OCF}-,$$
(with CF₃ substituents)

$$-\text{CF}_2\text{CF}_2\text{O}(\text{CF}_2)_4\text{OCF}_2\text{CF}_2-,$$

$$-\text{CF}_2\text{CF}_2\text{O}(\text{CF}_2)_4\text{OCFCF}_2\text{OCF}_2\text{CF}_2-,$$
(with CF₃ substituent)

$$-\text{CF}_2\text{CF}_2\text{OCF}_2\text{CFO}(\text{CF}_2)_4\text{OCFCF}_2\text{OCF}_2\text{CF}_2-.$$
(with CF₃ substituents)

-continued
or

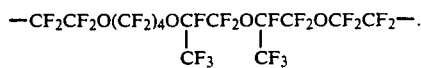

6. A compound according to claim 1, wherein $R^f$ is a perfluoroalkylene of 2-10 C atoms.

7. A compound according to claim 6, wherein $R^f$ is —C₂F₄—, —C₄F₈—, —C₆F₁₂— or —C₈F₁₆—.

8. A compound according to claim 1, wherein $R^1$ is methyl, ethyl or

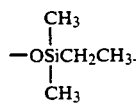

9. A compound according to claim 1, wherein $R^2$ is an alkylene group having 1-6 C atoms, an alkylene group having 1-6 atoms and a terminal oxygen atom, or an alkylene group having 1-6 C atoms and an intervening oxygen atom.

10. A compound according to claim 1, wherein $R^2$ is a divalent organic group containing an ester bond.

11. A compound according to claim 9, wherein $R^2$ is —(CH₂)₄—, —(CH₂)₂OCH₂—, —CH₂CH₂—, —(CH₂)₃O— or —(CH₂)₃OCH₂—.

12. A compound according to claim 1, wherein $R^f$ is a perfluoropolyether group of 4-15 carbon atoms, or a perfluoroalkylene group of 2-10 carbon atoms;

$R^1$ is methyl, ethyl or

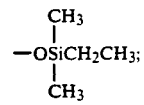

and $R^2$ is an alkylene group having 1-6 C atoms, an alkylene group having 1-6 C atoms and a terminal oxygen atom, or an alkylene group having 1-6 C atoms and an intervening oxygen atom.

13. A compound according to claim 1, wherein said compound is of the formulae

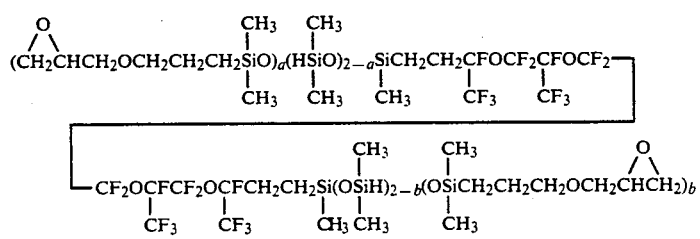

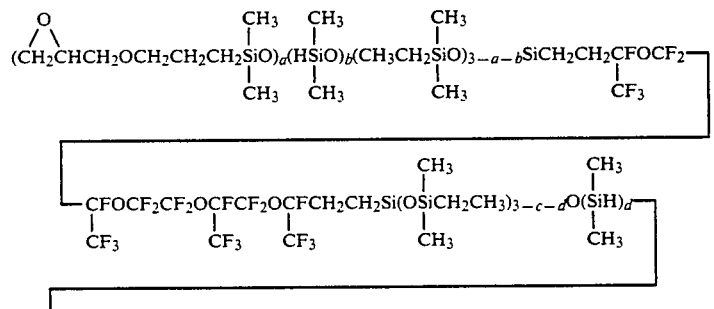

wherein a is 0-2, b is 0-2, and the sum of a+b is 2;

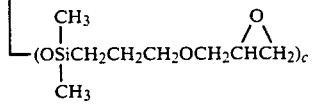

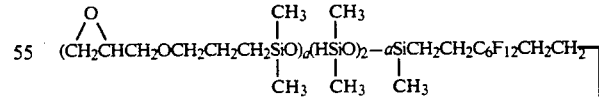

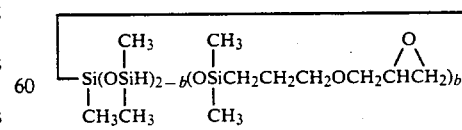

wherein a is 0-2, b is 0-2, c is 0-2, d is 0-2, a+c is 2, b+d is 2, the sum of a+b satisfies the equation $1 \leq a+b \leq 3$; and the sum of c+d satisfies the equation $1 \leq c+d \leq 3$; or

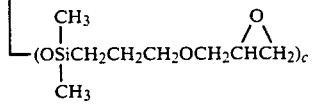

wherein a is 0-2, b is 0-2 and the sum of a+b is 2.

* * * * *